(12) United States Patent
Guo et al.

(10) Patent No.: US 10,606,982 B2
(45) Date of Patent: Mar. 31, 2020

(54) ITERATIVE SEMI-AUTOMATIC ANNOTATION FOR WORKLOAD REDUCTION IN MEDICAL IMAGE LABELING

(71) Applicant: INTERNATIONAL BUSINESS MACHINES CORPORATION, Armonk, NY (US)

(72) Inventors: Yufan Guo, San Jose, CA (US); Yaniv Gur, San Jose, CA (US); Mehdi Moradi, San Jose, CA (US)

( * ) Notice: Subject to any disclaimer, the term of this patent is extended or adjusted under 35 U.S.C. 154(b) by 161 days.

(21) Appl. No.: 15/697,341

(22) Filed: Sep. 6, 2017

(65) Prior Publication Data
US 2019/0073447 A1    Mar. 7, 2019

(51) Int. Cl.
*G06K 9/00* (2006.01)
*G06F 19/00* (2018.01)
(Continued)

(52) U.S. Cl.
CPC .......... *G06F 19/321* (2013.01); *G06F 17/241* (2013.01); *G06F 17/2785* (2013.01);
(Continued)

(58) Field of Classification Search
CPC ...... G06F 19/321; G06F 19/32; G06F 17/241; G06F 17/2785; G06F 3/0482; G06F 3/04845; G06F 3/04842; G06F 16/51; G06F 16/5866; G06F 16/24573; G06F 16/24575; G06F 16/9558; G06F 21/6254; G06K 9/6253; G06K 9/6267; G06K 9/46; G06K 9/4661; G06K 9/4676; G06K 9/6218; G06K 9/6254; G06K 9/6256; G06K 9/6284;
(Continued)

(56) References Cited

U.S. PATENT DOCUMENTS 8,934,722 B2    1/2015 Peleg et al.
9,122,955 B2    9/2015 Greenspan et al.
(Continued)

OTHER PUBLICATIONS

Carstens, "A Multiple Instance Learning Based Self Learning Approach to Reduce Human Effort in Marking Regions of Interest in Imaging Applications," Siemens, IP.com, IPCOM000213368D (Dec. 13, 2011).
(Continued)

*Primary Examiner* — Jose L Couso
(74) *Attorney, Agent, or Firm* — Erik Huestis; Stephen Kenny; Foley Hoag (57) ABSTRACT

Semi-automatic annotation of medical images is provided. In various embodiments, a classifier is applied to each of a first plurality of medical images to generate a label and an associated confidence value for each of the first plurality of medical images. The classifier is pre-trained using a manually labeled set of medical images. Those of the first plurality of medical images having an associated confidence value below a predetermined threshold are selected. The selected medical images are provided to a user. Updated labels are received from the user for the selected medical images. The classifier is retrained using the first plurality of medical images, with the updated labels for the selected medical images and the generated labels for medical images not selected.

20 Claims, 6 Drawing Sheets

(51) Int. Cl.
| | |
|---|---|
| *G06K 9/62* | (2006.01) |
| *G06F 17/24* | (2006.01) |
| *G16H 30/40* | (2018.01) |
| *G16H 50/20* | (2018.01) |
| *G06F 17/27* | (2006.01) |
| *G06F 3/0482* | (2013.01) |
| *G06N 5/00* | (2006.01) |
| *G06N 20/10* | (2019.01) |
| *G06N 20/20* | (2019.01) |
| *G06N 3/04* | (2006.01) |

(52) U.S. Cl.
CPC ......... *G06K 9/6253* (2013.01); *G06K 9/6263* (2013.01); *G06K 9/6267* (2013.01); *G16H 30/40* (2018.01); *G16H 50/20* (2018.01); *G06F 3/0482* (2013.01); *G06N 3/04* (2013.01); *G06N 5/003* (2013.01); *G06N 20/10* (2019.01); *G06N 20/20* (2019.01)

(58) Field of Classification Search
CPC ............ G06K 2009/4666; A61B 5/015; A61B 5/0013; A61B 6/503; A61B 6/5217; A61B 6/468; A61B 2576/00; G06N 3/0454; G06N 3/084; G06N 3/086; G06T 3/0056; G06T 7/0012; G06T 7/38; G06T 7/33; G06T 7/35; G06T 7/97; G06T 2207/30048; G06T 2207/30061; G06T 2207/20076; G06T 2210/41; G06T 2219/004; G16H 30/20; G16H 30/40; G16H 30/00; G16H 50/20; G16H 50/00; G16H 50/30; G16H 50/50; G16H 50/70; G16H 50/80; G16H 80/00; G16H 15/00; B25J 9/163; B25J 9/1671; G01R 33/5608; G05B 2219/39004; G09B 23/28; G09G 2380/08; Y10S 128/922
See application file for complete search history.

(56) References Cited

U.S. PATENT DOCUMENTS

| | | | |
|---|---|---|---|
| 9,324,022 | B2 | 4/2016 | Williams, Jr. et al. |
| 9,536,054 | B1* | 1/2017 | Podilchuk ............ G06T 7/0012 |
| 10,140,421 | B1* | 11/2018 | Bernard ............... G06F 19/321 |
| 2005/0010445 | A1* | 1/2005 | Krishnan ............. G06F 19/321 |
| | | | 705/2 |
| 2012/0027271 | A1* | 2/2012 | Zankowski ............ G06T 7/143 |
| | | | 382/128 |
| 2012/0283574 | A1 | 11/2012 | Park et al. |
| 2015/0086133 | A1* | 3/2015 | Grady ................. G06F 16/5866 |
| | | | 382/278 |
| 2015/0205917 | A1* | 7/2015 | Mabotuwana ........ G06F 19/321 |
| | | | 382/128 |
| 2016/0292856 | A1* | 10/2016 | Niemeijer ............ G06T 7/0012 |
| 2016/0364544 | A1* | 12/2016 | Das ...................... A61B 5/7267 |
| 2017/0200268 | A1* | 7/2017 | Podilchuk ............ G06K 9/6232 |
| 2018/0012359 | A1* | 1/2018 | Prentasic .............. G06T 7/0014 |
| 2018/0025255 | A1* | 1/2018 | Poole ................... G06K 9/6277 |
| | | | 382/131 |
| 2019/0096060 | A1* | 3/2019 | Zhang .................. G06T 7/0012 |
| 2019/0223845 | A1* | 7/2019 | Podilchuk .......... A61B 10/0041 |

OTHER PUBLICATIONS

Maier-Hein et al., Can masses of non-experts train highly accurate image classifiers? A crowdsourcing approach to instrument segmentation in laparoscopic images, Med Image Comput Comput Assist Interv, 17(Pt 2):438-445 (2014).

Moradi et al., "A cross-modality neural network transform for semi-automatic medical image annotation," Miccai 2016, pp. 300-307 (2016).

Su et al., "Interactive cell segmentation based on active and semi-supervised learning," IEEE T Med Imaging, 35(3):762-777 (2016).

Syeda-Mahmood et al., "Identifying patients at risk for aortic stenosis through learning from multimodal data," Miccai 2016, pp. 238-245 (2016).

Vajda et al., "Label the many with a few: Semiautomatic medical image modality discovery in a large image collection," 2014 IEEE Symposium on Computational Intelligence in Healthcare and e-health (CI-CARE), pp. 1-7 (Dec. 2014).

Zamacona et al., "Reducing classification cost through strategic annotation assignment," 2013 IEEE 13th International Conference on Data Mining Workshops, IEEE Computer Society, pp. 287-294 (2013).

Zhu, "Semi-supervised learning literature survey," University of Wisconsin—Madison (Jul. 19, 2008).

Krizhevsky, A., Sutskever, I., Hinton, G.E.: Imagenet classificatio n with deep convolutional neural networks. In: Pereira, F., Burges, C.J.C., Bottou, L., Weinberger, K.Q. (eds.) Advances in Neural Information Processing Systems 25, pp. 1097-1105. Curran Associate s, Inc. (2012).

* cited by examiner

ITERATIVE SEMI-AUTOMATIC ANNOTATION FOR WORKLOAD REDUCTION IN MEDICAL IMAGE LABELING

BACKGROUND

Embodiments of the present disclosure relate to semi-automatic annotation of medical images, and more specifically, to iterative semi-automatic annotation for workload reduction in medical image labeling.

BRIEF SUMMARY

According to embodiments of the present disclosure, methods of and computer program products for semi-automatic annotation of medical images are provided. In various embodiments, a classifier is applied to each of a first plurality of medical images to generate a label and an associated confidence value for each of the first plurality of medical images. The classifier is pre-trained using a manually labeled set of medical images. Those of the first plurality of medical images having an associated confidence value below a predetermined threshold are selected. The selected medical images are provided to a user. Updated labels are received from the user for the selected medical images. The classifier is retrained using the first plurality of medical images, with the updated labels for the selected medical images and the generated labels for medical images not selected.

DETAILED DESCRIPTION

Machine learning is useful in a variety of real-world applications. In certain tasks, it enables machine performance at or even above a human level. However, to build robust and accurate machine learning solutions, large amounts of data need to be curated and labeled. While in many applications, such as image and speech recognition, large collections of labeled data can be obtained through crowd-sourcing over the Web, in the medical domain the situation is different.

Machine learning can aid clinicians by providing accurate diagnosis faster than before. However, the penetration of machine learning into the medical field has been slowed by a lack of high-quality labeled data. Because medical data are collected in the course of routine clinical practice and are subject to security and privacy restrictions, availability is limited. Medical data must also be labeled by experts. Unlike in other domains, medical expert resources are scarce and costly.

To address these and other shortcomings of alternative approaches, the present disclosure provides semi-supervised algorithms to reduce the number of annotated training images needed to achieve a given level of classification accuracy. Solutions provided herein combine active learning and self training. Some embodiments, employ a web-based annotation platform for expert labeling. The subject matter provided herein improves the efficiency of data preparation, irrespective of the classifier employed. Manual labeling effort is reduced through the user of a trained classifier. In one exemplary ultrasound mode labeling embodiment described below, a classifier accuracy of 98% is achieved while reducing the manual labeling effort to 4% of an unlabeled samples set.

Figure 1:
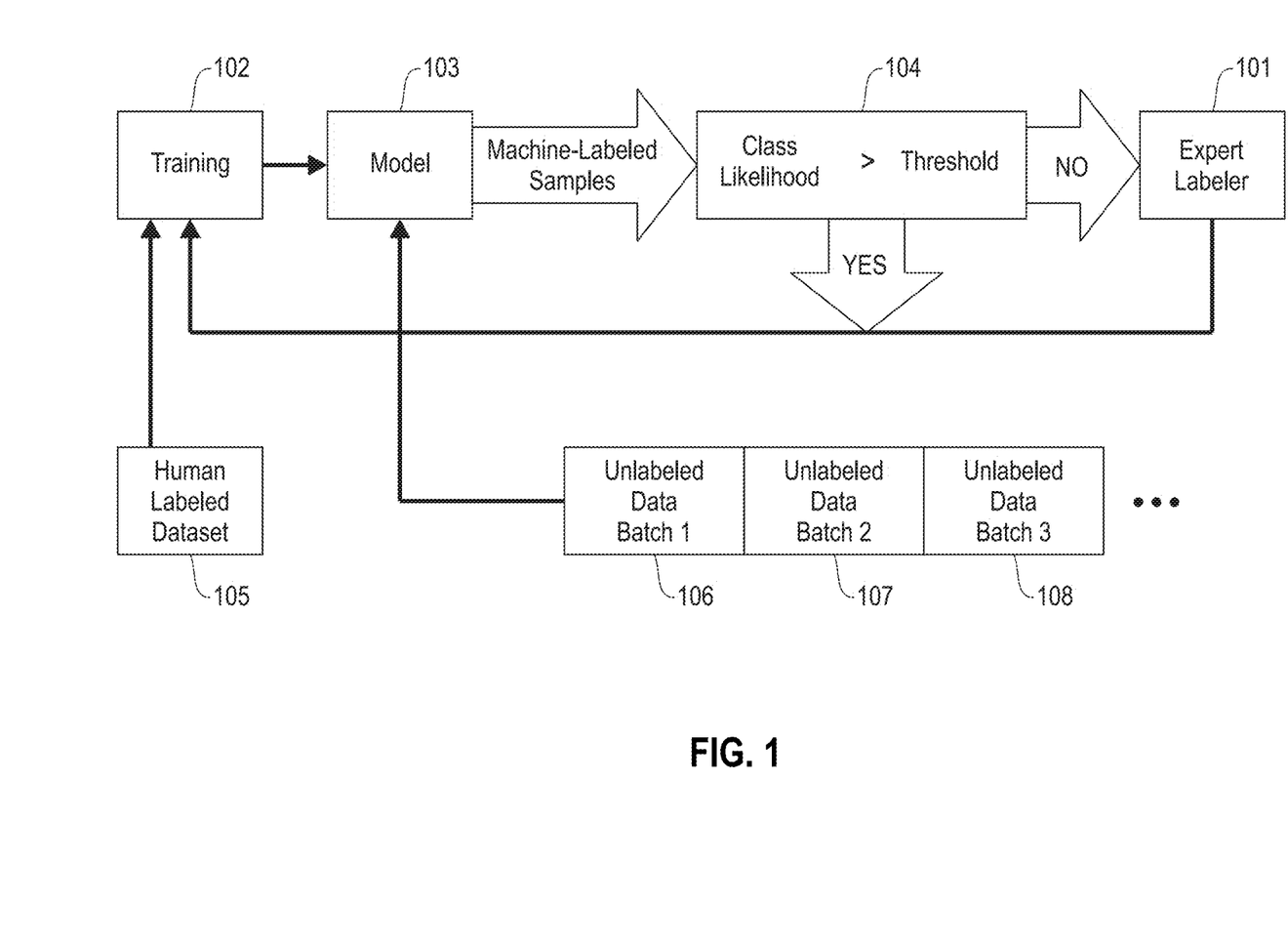
FIG. 1 illustrates an algorithm for semi-automatic labeling according to various embodiments of the present disclosure.

Referring now to FIG. 1, an algorithm for semi-automatic labeling is illustrated according to various embodiments. As described further below, an iterative process is provided of labeling 101, training a classifier 102, and testing 103 . . . 104. A small set of labeled images 105 is used at the start, complemented with human labeling of difficult test cases at each iteration.

As compared to applying active learning or self-training alone, the present disclosure provides methods for using all the available data to achieve high classifier accuracy while dramatically reducing manual labeling effort. In general, active learning may provide a semi-supervised approach to machine learning that addresses the problem of labeling large datasets while reducing manual labeling effort. An iterative process of training, prediction, and sample selection for manual labeling is employed. In active learning, only manually labeled data are used to train a classifier. In general, in self-training, a classifier is trained on classifier-labeled data.

An initial small set 105 of labeled images $\mathcal{T}_0 = \{(x_i, y_i) | i=1, \ldots, N_0\}$ is provided, where $N_0$ is the number of samples, and $y_i$ is the label of sample $x_i$. A classifier is trained 102 using $\mathcal{T}_0$ to produce a model 103 $M_0$. The model accuracy is tested in all the steps on a separate and fixed validation set, $\mathcal{V}$. A larger dataset of $N_1$ unlabeled samples 106 . . . 108, where $S_1 = \{(x_i, ?) | i=1, \ldots, N_1\}$. As set out below, an improved classifier is built using this dataset, without needing to manually label all of the samples.

Initially, $S_1$ is automatically labeled using $M_0$ (at 103), where the output is a label $M_0(x_i) = y_i$ and a vector of class likelihoods per sample as illustrated in Equation 1, where k is the number of classes in the problem.

$$\mathcal{P}_{(y_i | x_i)} = \{P(y_i = 0 | x_i), P(y_i = 1 | x_1), \ldots, P(y_i = k-1 | x_i)\} \quad \text{Equation 1}$$

A subset of samples is selected for manual annotation by looking at the class likelihoods (at 104). All the samples with the largest class likelihood below a threshold $t \in (0,1)$, that is, $\max(P(y_i | x_i)) < t$, are considered as hard cases and selected for manual labeling (at 101), while labels with a class likelihood above the threshold are accepted as correct labels. For each of the hard cases, the predicted label is presented to an annotator, for example via a web-based annotation platform, to accept or change. Once the manual labeling is completed, all the labels are combined to form a fully labeled set $S_1$.

A new training set $\mathcal{D}_1 = \mathcal{D}_0 \cup S_1$ is created, and a learned model $M_1$ is produced, which is used to label a new set of unlabeled samples $S_2$. It will be appreciated that the new learned model may be generated by further training the existing classifier reflecting $M_0$, or by training a newly instantiated classifier. It will be appreciated that a variety of trainable classifiers are suitable for use according to the present disclosure, including random decision forests, including linear classifiers, logistic regression, support vector machines (SVM), or artificial neural networks (ANN) such as recurrent neural networks (RNN) or convolutional neural network (CNN).

The process of labeling new sets in a semi-automatic fashion followed by re-training is repeated every time more data become available, or until the classifier reaches a desired accuracy on the validation set. In various embodiments, available data is divided into batches, and the active learning cycle is iterated on the batches while monitoring the performance on an independent validation set. It will be appreciated that the validation set should include equally distributed representatives from all the classes in the problem in order to achieve high accuracy. As noted above, the present approach is not specific to one type classifier. Any trainable classifier that provides class likelihood measures is suitable for use according to the present disclosure.

Figure 2:
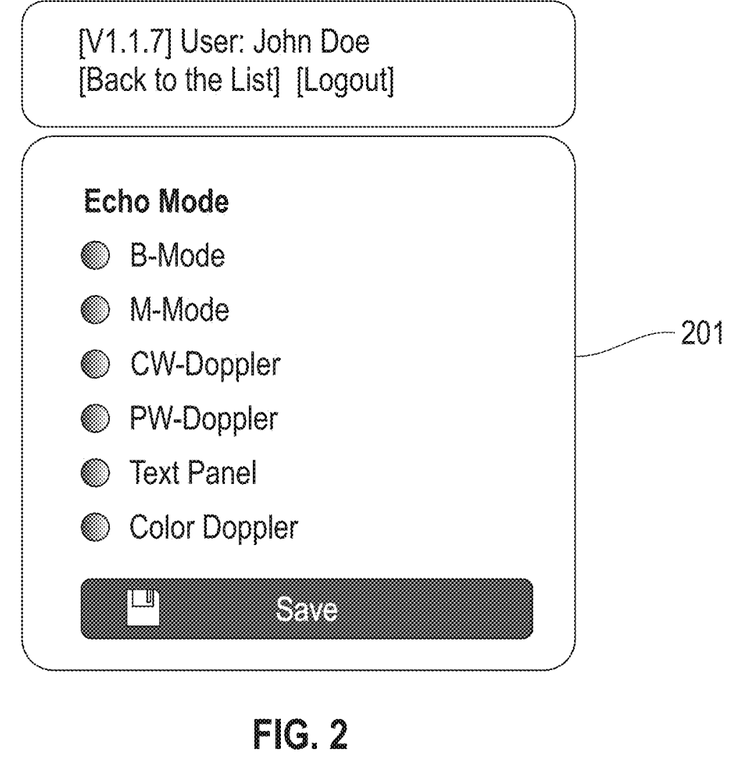
FIG. 2 illustrates an exemplary user interface for medical image labeling according to embodiments of the present disclosure.

Referring now to FIG. 2, an exemplary user interface for ultrasound labeling is illustrated. In various embodiments, a web-based annotation platform is used to present images for annotation to a user. In this example, the annotator views the images, and label them by selecting the correct ultrasound mode from menu 201 and saving. In this example, 6 classes are reflected: B-mode, M-mode, PW-Doppler, CW-Doppler, color-Doppler, and text-panel.

In a cardiac echo exam, sonographers collect images of a variety of modes. Ultrasound mode in not always recorded in the DICOM header, but it needs to be detected for further analysis by systems that perform archival analysis of medical images.

Accordingly, in an exemplary embodiment, a convolutional neural network (CNN) is provided for classifying a given image in one of six possible modes: B-Mode, M-Mode, PW-Doppler, CW-Doppler, Color-Doppler, and text-panels. In this example, a dataset of 980 images labeled by clinicians provides an initial dataset. This dataset was used to generate the initial learned model by training Alex-Net after reducing the number of network outputs to 6. The network was trained for 30 epochs with a batch size of 128 images, and was validated on a dataset of 3,502 samples pre-labeled by clinicians.

Figure 3A:
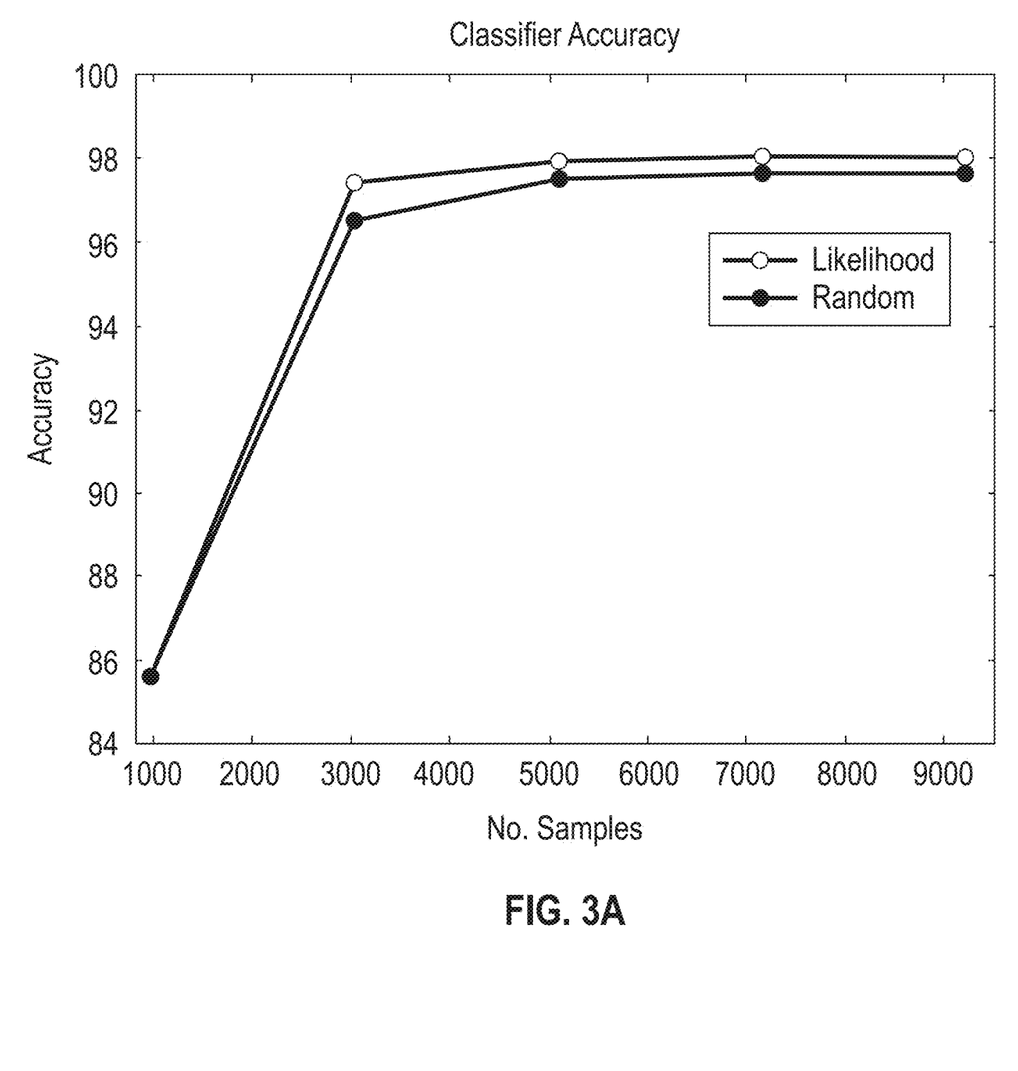
FIG. 3A is a graph of accuracy relative to number of samples, illustrating the accuracy of semi-automatic labeling according to embodiments of the present disclosure as compared to random sampling.

Referring to FIG. 3A, the results of semi-automatic labeling with likelihood-based sampling according to the present disclosure are compared to random sampling. The CNN model accuracy is plotted as a function of the number of training samples. In random sampling, the classifier accuracy converged to 97.6% as compared to 98% following the approach described herein.

Figure 3B:
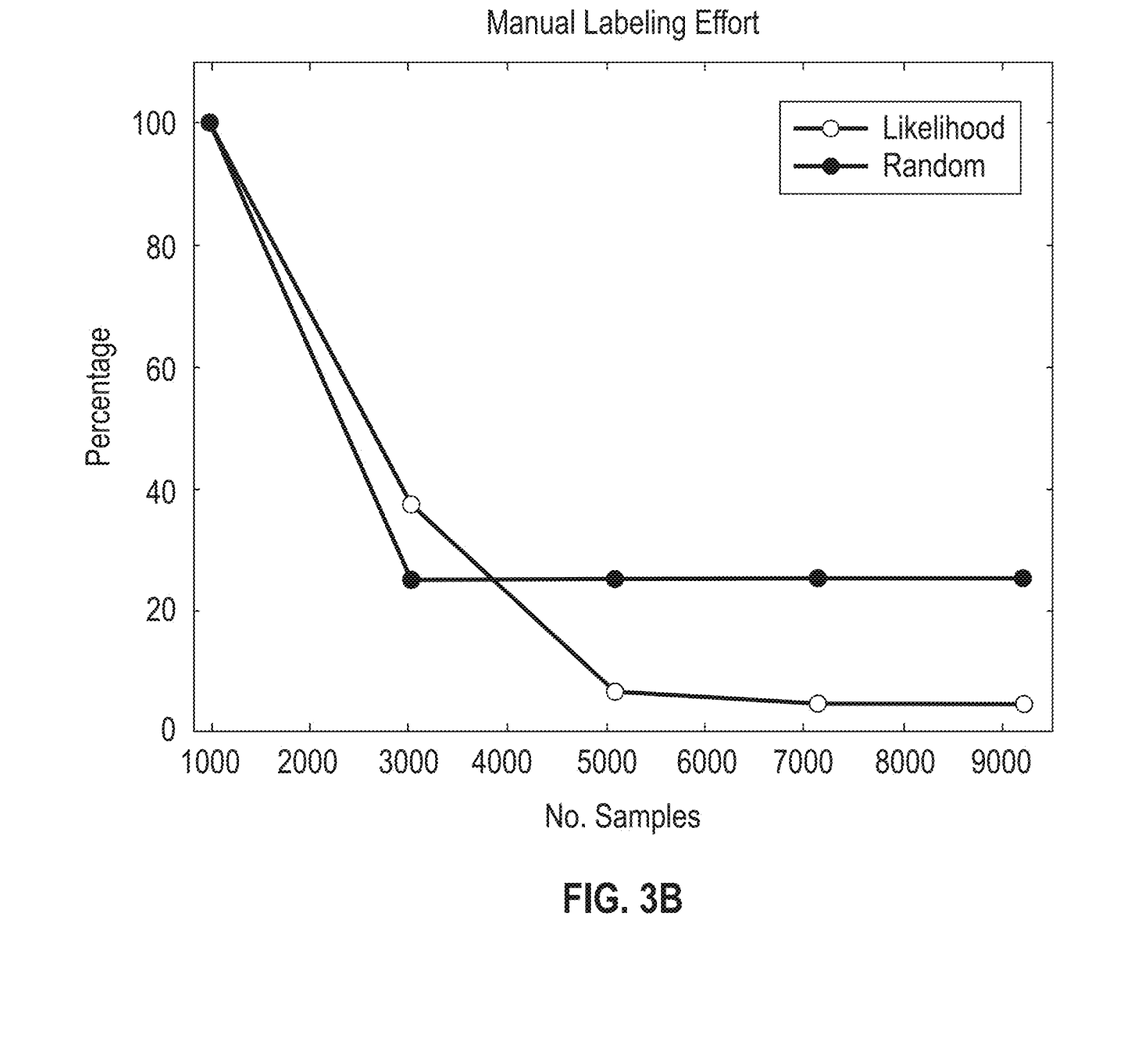
FIG. 3B is a graph of manual labeling effort relative to number of samples, illustrating the performance of semi-automatic labeling according to embodiments of the present disclosure as compared to random sampling.

Referring to FIG. 3B, the percentage of manually labeled samples in each iteration are compared according to selection criteria. The manual labeling rate using likelihood selection as set out herein dropped from 100% in the initial set to only 4%.

The measured accuracy of the initial network trained on 980 manually labeled samples was 85.6% when tested on the independent validation set. Semi-automatic labeling was performed on equal size datasets consisting of 2060 images each. Each iteration following the process described above with regard to FIG. 1. That is, one batch of 2060 images was automatically labeled using the model produced in the previous iteration. Then, the samples with class likelihood of less than 0.9 were selected for manual labeling. Labels with likelihood above that threshold were accepted. After any misclassifications of hard cases were corrected, a new training set was formed by combining the new labeled samples (both hard cases and network-labeled cases) with the training set from the previous iteration, and the network was retrained.

This process was repeated until all 4 datasets were labeled. After retraining with the first set of semi-automatically labeled samples, the classifier reached an accuracy of 97.4% that stabilized at 98% after the third labeling iteration. Moreover, the number of samples selected by the class likelihood criterion for manual labeling dropped dramatically from around 36% (771 samples) at the first iteration, to around 4% (85 samples) at the last iteration. Thus, by using this approach the labeling workload was reduced by a factor of 25 without compromising the accuracy. For reference, the likelihood-based sampling strategy is compared to random sampling at a constant rate of 25%. The strategy described herein outperformed random sampling and converged to a higher classifier accuracy with less manual labeling effort.

In another exemplary embodiment, a support vector machine (SVM) classifier is provided for classifying patients for the presence of aortic stenosis, based on noisy measurements of maximum blood flow velocity and pressure gradient through the aortic valve, extracted from archival sources and automatic analysis of CW Doppler images. The classifier used in this example was a binary SVM, trained on a nine dimensional feature vector. Nine hundred cases were available for the training phase of this experiment, along with an additional 100 cases solely used for testing. The SVM model was initially trained on 5 cases and data was added in batches of size 20.

In this example, the initial accuracy of stenosis detection for the classifier was 72%. After reaching 200 training samples, the classification accuracy saturated at 93%. Compared to labeling and adding training data randomly without considering class likelihoods, the same level of accuracy was achieved only after all 900 samples were labeled and included in training. In other words, the algorithms described herein reduced the labeling effort by 78%.

Figure 4:
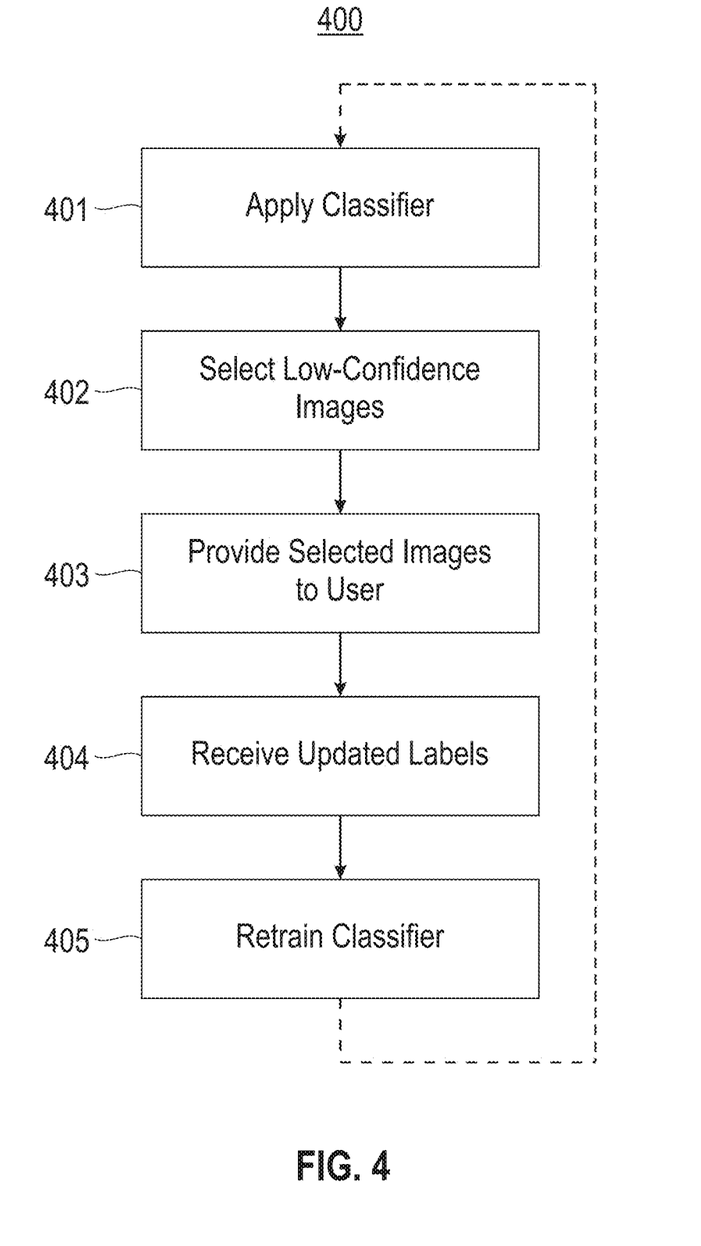
FIG. 4 illustrates a method for semi-automatic annotation of medical images according to embodiments of the present disclosure.

With reference now to FIG. 4, a method for semi-automatic annotation of medical images is illustrated according to embodiments of the present disclosure. At 401, a classifier is applied to each of a first plurality of medical images to generate a label and an associated confidence value for each of the first plurality of medical images. The classifier is pre-trained using a manually labeled set of medical images. At 402, those of the first plurality of medical images having an associated confidence value below a predetermined threshold are selected. At 403, the selected medical images are provided to a user. At 404, updated labels are received from the user for the selected medical images. At 505, the classifier is retrained using the first plurality of medical images, with the updated labels for the selected medical images and the generated labels for medical images not selected.

As described above, the present disclosure addresses the problem of annotating large collections of medical images. In ultrasound mode labeling, the teachings of the present disclosure achieve a classifier accuracy of 98% while reducing the manual labeling effort to 4% of an unlabeled samples set. In various embodiments, systems and methods described herein may be integrated into a web-based platform for expert sourcing of annotation tasks.

Figure 5:
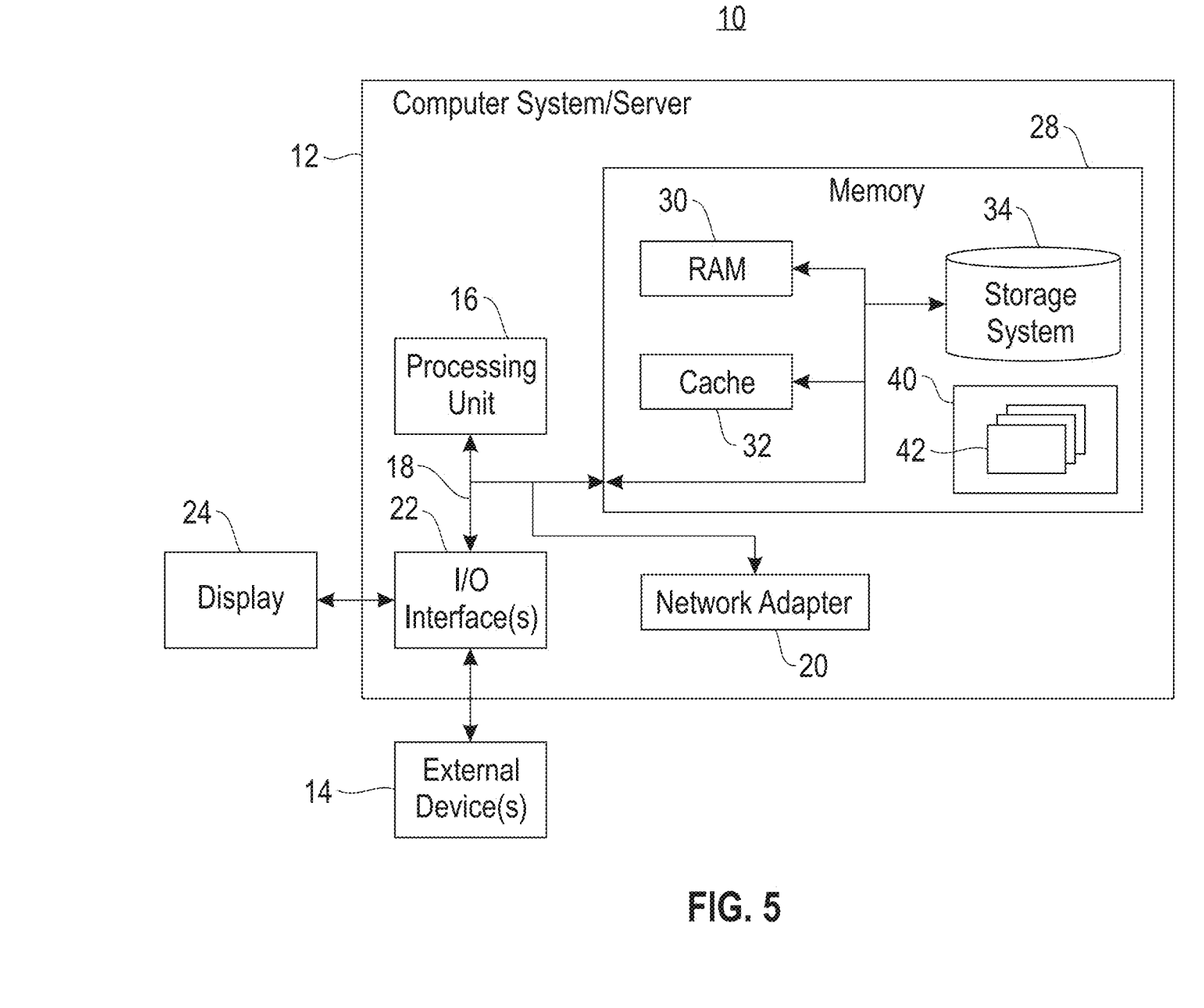
FIG. 5 depicts a computing node according to an embodiment of the present invention.

Referring now to FIG. 5, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    applying a classifier to each of a first plurality of medical images to generate a label and an associated confidence value for each of the first plurality of medical images, resulting in generated labels and associated confidence values, the classifier being pre-trained using a manually labeled set of medical images;
    selecting those of the first plurality of medical images having an associated confidence value below a predetermined threshold, resulting in selected medical images;
    providing the selected medical images to a user;
    receiving from the user updated labels for the selected medical images;
    retraining the classifier using the first plurality of medical images, with the updated labels for the selected medical images and the generated labels for medical images not selected.

2. The method of claim 1, wherein said retraining uses the manually labeled set of medical images.

3. The method of claim 1, wherein the classifier comprises a random decision forest, a linear classifier, logistic regression, a support vector machine, or an artificial neural network.

4. The method of claim 1, further comprising:
retraining the classifier using additional sets of medical images and user-updated labels until the classifier achieves a predetermined accuracy.

5. The method of claim 1, further comprising:
for a superset of medical images comprising the first plurality of medical images, dividing the superset of medical images into the first plurality of medical images and additional sets of medical images;
retraining the classifier using the additional sets of medical images and user-updated labels until the classifier has been trained on all medical images in the superset.

6. The method of claim 1, wherein providing the selected medical images to a user comprises displaying the selected medical images via a web interface.

7. The method of claim 1, wherein receiving from the user updated labels comprises receiving a selection from among a plurality of predetermined labels.

8. A system comprising:
a data store comprising a first plurality of medical images;
a computing node comprising a computer readable storage medium having program instructions embodied therewith, the program instructions executable by a processor of the computing node to cause the processor to perform a method comprising:
applying a classifier to each of the first plurality of medical images to generate a label and an associated confidence value for each of the first plurality of medical images, resulting in generated labels and associated confidence values, the classifier being pre-trained using a manually labeled set of medical images;
selecting those of the first plurality of medical images having an associated confidence value below a predetermined threshold, resulting in selected medical images;
providing the selected medical images to a user;
receiving from the user updated labels for the selected medical images;
retraining the classifier using the first plurality of medical images, with the updated labels for the selected medical images and the generated labels for medical images not selected.

9. The system of claim 8, wherein said retraining uses the manually labeled set of medical images.

10. The system of claim 8, wherein the classifier comprises a random decision forest, a linear classifier, logistic regression, a support vector machine, or an artificial neural network.

11. The system of claim 8, the method further comprising:
retraining the classifier using additional sets of medical images and user-updated labels until the classifier achieves a predetermined accuracy.

12. The system of claim 8, the method further comprising:
for a superset of medical images comprising the first plurality of medical images, dividing the superset of medical images into the first plurality of medical images and additional sets of medical images;
retraining the classifier using the additional sets of medical images and user-updated labels until the classifier has been trained on all medical images in the superset.

13. The system of claim 8, wherein providing the selected medical images to a user comprises displaying the selected medical images via a web interface.

14. The system of claim 8, wherein receiving from the user updated labels comprises receiving a selection from among a plurality of predetermined labels.

15. A computer program product for semi-automatic annotation of medical images, the computer program product comprising a computer readable storage medium having program instructions embodied therewith, the program instructions executable by a processor to cause the processor to perform a method comprising:
applying a classifier to each of a first plurality of medical images to generate a label and an associated confidence value for each of the first plurality of medical images, resulting in generated labels and associated confidence values, the classifier being pre-trained using a manually labeled set of medical images;
selecting those of the first plurality of medical images having an associated confidence value below a predetermined threshold, resulting in selected medical images;
providing the selected medical images to a user;
receiving from the user updated labels for the selected medical images;
retraining the classifier using the first plurality of medical images, with the updated labels for the selected medical images and the generated labels for medical images not selected.

16. The computer program product of claim 15, wherein said retraining uses the manually labeled set of medical images.

17. The computer program product of claim 15, wherein the classifier comprises a random decision forest, a linear classifier, logistic regression, a support vector machine, or an artificial neural network.

18. The computer program product of claim 15, the method further comprising:
retraining the classifier using additional sets of medical images and user-updated labels until the classifier achieves a predetermined accuracy.

19. The computer program product of claim 15, the method further comprising:
for a superset of medical images comprising the first plurality of medical images, dividing the superset of medical images into the first plurality of medical images and additional sets of medical images;
retraining the classifier using the additional sets of medical images and user-updated labels until the classifier has been trained on all medical images in the superset.

20. The computer program product of claim 15, wherein providing the selected medical images to a user comprises displaying the selected medical images via a web interface.

* * * * *